(12) United States Patent
Kinoshita et al.

(10) Patent No.: US 10,639,249 B2
(45) Date of Patent: May 5, 2020

(54) REDUCTION TREATMENT AGENT, REDUCTION COSMETIC, REDUCTION FOOD AND METHOD FOR PRODUCING REDUCTION TREATMENT AGENT

(71) Applicants: Eiko Kinoshita, Kyoto-shi, Kyoto (JP); Tatehiko Ogawa, Kyoto-shi, Kyoto (JP); Irene Fan, Tenafly, NJ (US)

(72) Inventors: Eiko Kinoshita, Kyoto (JP); Tatehiko Ogawa, Kyoto (JP)

(73) Assignees: Eiko Kinoshita, Kyoto (JP); Tatehiko Ogawa, Kyoto (JP); Irene Fan, Tenafly, NJ (US)

( * ) Notice: Subject to any disclaimer, the term of this patent is extended or adjusted under 35 U.S.C. 154(b) by 27 days.

(21) Appl. No.: 15/511,791

(22) PCT Filed: Sep. 24, 2015

(86) PCT No.: PCT/JP2015/076908
§ 371 (c)(1),
(2) Date: Mar. 16, 2017

(87) PCT Pub. No.: WO2016/047680
PCT Pub. Date: Mar. 31, 2016

(65) Prior Publication Data
US 2017/0296446 A1    Oct. 19, 2017

(30) Foreign Application Priority Data

Sep. 25, 2014   (JP) ................. 2014-194753

(51) Int. Cl.
| | | |
|---|---|---|
| *A61K 8/19* | (2006.01) | |
| *A01N 3/00* | (2006.01) | |
| *A61K 8/27* | (2006.01) | |
| *A61K 8/365* | (2006.01) | |
| *A61Q 19/00* | (2006.01) | |
| *A61Q 17/04* | (2006.01) | |
| *A01N 37/36* | (2006.01) | |
| *B22F 1/00* | (2006.01) | |
| *A01N 59/06* | (2006.01) | |
| *A01N 43/08* | (2006.01) | |
| *A01N 59/16* | (2006.01) | |
| *A61K 8/02* | (2006.01) | |
| *C02F 1/68* | (2006.01) | |
| *A23L 33/10* | (2016.01) | |
| *A23L 33/16* | (2016.01) | |

(Continued)

(52) U.S. Cl.
CPC .............. *A61K 8/19* (2013.01); *A01N 3/00* (2013.01); *A01N 37/36* (2013.01); *A01N 43/08* (2013.01); *A01N 59/06* (2013.01); *A01N 59/16* (2013.01); *A23L 33/10* (2016.08); *A23L 33/16* (2016.08); *A61K 8/022* (2013.01); *A61K 8/0241* (2013.01); *A61K 8/06* (2013.01); *A61K 8/27* (2013.01); *A61K 8/365* (2013.01); *A61K 8/676* (2013.01); *A61Q 17/04* (2013.01); *A61Q 19/00* (2013.01); *A61Q 19/02* (2013.01); *A61Q 19/10* (2013.01); *B22F 1/0059* (2013.01); *B22F 1/0062* (2013.01); *C02F 1/68* (2013.01); *C02F 1/705* (2013.01); *A23V 2002/00* (2013.01); *A61K 2800/10* (2013.01); *A61K 2800/612* (2013.01); *A61Q 1/02* (2013.01); *B22F 9/04* (2013.01); *B22F 2009/042* (2013.01); *B22F 2301/058* (2013.01); *B22F 2998/10* (2013.01); *C02F 1/50* (2013.01)

(58) Field of Classification Search
CPC .......... A01N 3/00; A01N 37/36; A01N 43/08; A01N 59/06; A01N 59/16; A23L 33/10; A23L 33/16; A23V 2002/00; A61K 8/19; A61K 8/27; A61K 8/365; A61K 8/0241; A61K 8/022; A61K 8/06; A61K 8/676; A61K 2800/612; A61K 2800/10; A61Q 17/04; A61Q 19/00; A61Q 19/02; A61Q 19/10; A61Q 1/02; B22F 1/0059; B22F 1/0062; B22F 2998/10; B22F 2009/042; B22F 9/04; B22F 2301/058; C02F 1/68; C02F 1/705; C02F 1/50
See application file for complete search history.

(56) References Cited

FOREIGN PATENT DOCUMENTS

| CN | 101422729 A | 5/2009 |
|---|---|---|
| JP | 2001-518111 A | 10/2001 |

(Continued)

OTHER PUBLICATIONS

May 30, 2017 Office Action issued in Japanese Patent Application No. 2016-550356.

(Continued)

Primary Examiner — Mina Haghighatian
Assistant Examiner — Nathan W Schlientz
(74) Attorney, Agent, or Firm — Oliff PLC

(57) ABSTRACT

A reduction treatment agent made of a powder with a particle size within a range of 1500 to 3000 mesh, the powder containing: 20 to 40 parts of a mixed-oxide powder containing magnesium oxide and zinc oxide; and 60 to 80 parts of an organic acid powder containing calcium, ascorbic acid, citric acid and salt. The reduction treatment agent may further contain one to six kinds of metal powder selected from the group of copper, molybdenum, nickel, cobalt, iron and aluminum, each in an amount of one part. Due to this configuration, the reduction treatment agent can be easily mixed with various substances when added to those substances. Even if the target substance is not water, the agent can entirely and uniformly change that substance into a reduced state. Additionally, the reduction treatment agent can act as a surfactant, and therefore, can be used as cosmetics or food.

5 Claims, 1 Drawing Sheet

(51) Int. Cl.
    *A61K 8/06*     (2006.01)
    *A61K 8/67*     (2006.01)
    *A61Q 19/02*     (2006.01)
    *A61Q 19/10*     (2006.01)
    *C02F 1/70*     (2006.01)
    *C02F 1/50*     (2006.01)
    *B22F 9/04*     (2006.01)
    *A61Q 1/02*     (2006.01)

(56) References Cited

FOREIGN PATENT DOCUMENTS

| | | |
|---|---|---|
| JP | 2002-348208 A | 12/2002 |
| JP | 2005-162655 A | 6/2005 |
| JP | 2005-232015 A | 9/2005 |
| JP | 2006-008631 A | 1/2006 |
| JP | 2009-126736 A | 6/2009 |
| JP | 2009-131825 A | 6/2009 |
| JP | 2010-527332 A | 8/2010 |
| JP | 2011-255360 A | 12/2011 |
| JP | 2013-212498 A | 10/2013 |
| JP | 2015-042618 A | 3/2015 |
| JP | 2015-093211 A | 5/2015 |
| JP | 2015-199672 A | 11/2015 |
| WO | 98/42300 A1 | 10/1998 |
| WO | 2008/138894 A2 | 11/2008 |

OTHER PUBLICATIONS

Dec. 15, 2015 Search Report issued in International Patent Application No. PCT/JP2015/076908.
Dec. 15, 2015 Written Opinion issued in International Patent Application No. PCT/JP2015/076908.
Aug. 15, 2017 Office Action issued in Japanese Application No. 2016-550356.
Aug. 8, 2018 Office Action issued in Korean Patent Application No. Oct. 2017-7010806. X.
Mar. 2018 Office Action issued in Korean Patent Application N. 10-2017-7010806.

REDUCTION TREATMENT AGENT, REDUCTION COSMETIC, REDUCTION FOOD AND METHOD FOR PRODUCING REDUCTION TREATMENT AGENT

TECHNICAL FIELD

The present invention relates to a reduction treatment agent which changes a target substance into a reduced state when added to the substance, as well as a reduction cosmetic and reduction food.

BACKGROUND ART

One of the indices used for quantitatively evaluating the tendency of a substance to release or receive electrons is the oxidization reduction potential (ORP). A substance having a higher ORP is more likely to oxidize other substances, while a substance having a lower ORP is more likely to reduce other substances. The intermediate value of the ORP is considered to be +200 mV. Water whose ORP is lower than this middle value is called the "reduction water". Since living organisms are normally in a reduced state, reduction water presents less of a burden on living organisms. For this reason, reduction water has been used as healthy drinking water as well as in various other forms, such as bath agents, lotions and external skin agents (see Patent Literatures 1-4).

For example, reduction water is produced by placing an amount of water in a container with an anode and cathode arranged in it, and passing electric current through the water with the potential between the anode and cathode maintained below +200 mV. In another method, an amount of water is poured into a container with a catalyst placed in it, and electric current is similarly passed to make hydrogen generated from the catalyst, whereby reduction water (hydrogen reduction water) is produced (Patent Literature 5).

However, any of these methods requires time to produce a sufficient amount of reduction water. Furthermore, the produced reduction water must be immediately used, because it is difficult to maintain hydrogen for a long period of time in a dissolved form in the water.

In view of these problems, a powdery reduction treatment agent, called the "reduction powder", has been provided (Patent Literature 6). Reduction powder is principally made from metal that easily generates hydrogen (zinc, iron, magnesium, copper and/or potassium), with the additional constituents of calcium, sodium, molybdenum, vanadium, nickel, manganese, selenium, cobalt, lithium, phosphorus and chromium. Adding reduction powder to tap water or a water-containing substance changes the target substance into a reduced state within a short period of time. Furthermore, reduction powder can be stored for a long period of time.

CITATION LIST

Patent Literature

Patent Literature 1: JP 2002-348208 A
Patent Literature 2: JP 2005-162655 A
Patent Literature 3: JP 2005-232015 A
Patent Literature 4: JP 2006-008631 A
Patent Literature 5: JP 2009-131825 A
Patent Literature 6: JP 2013-212498 A

SUMMARY OF INVENTION

Technical Problem

Upon coming in contact with water, reduction powder generates active hydrogen. This active hydrogen changes the target substance into a reduced state by its reducing action. Accordingly, in order to entirely change the target substance into a reduced state by the addition of the reduction powder to the same substance, it is necessary to uniformly disperse the reduction powder over the entire target substance. However, it is difficult to uniformly disperse the reduction powder disclosed in Patent Literature 6 over the entire target substance if the target substance is a substance having a comparatively high degree of viscosity, such as a milky lotion, hand cream or ointment.

The problem to be solved by the present invention is to provide a reduction treatment agent which can be easily mixed with various substances when added to those substances, as well as a reduction cosmetic and reduction food.

Solution to Problem

The reduction treatment agent according to the present invention developed for solving the previously described problem is made of a powder having a particle size within a range of 1500 to 3000 mesh, the powder containing:

a) 20 to 40 parts of a mixed-oxide powder containing magnesium oxide and zinc oxide; and b) 60 to 80 parts of an organic acid powder containing calcium, ascorbic acid, citric acid and salt.

In the aforementioned reduction treatment agent, either the ascorbic acid or citric acid may be omitted. In addition to the two kinds of metal of magnesium and zinc, one to six kinds of metal powders selected from the group of copper, molybdenum, nickel, cobalt, iron and aluminum may also be added. When necessary, a metal powder different from the previously listed ones may also be added. In the case of adding one or more metal powders other than magnesium and zinc (those powders are hereinafter called the "additional metal powders"), it is preferable to add each kind of additional metal powder in an amount of one part for 80 parts of magnesium and 15 parts of zinc.

The reduction treatment agent according to the present invention can be produced by the following method.

That is to say, the method for producing a reduction treatment agent according to the present invention includes the following processes a) through g):

a) 80 parts of magnesium and 20 parts of zinc are pulverized into a mixed powder with a particle size of approximately 200 to 400 mesh. For this pulverizing process, a small amount of olive oil or vitamin E oil may preferably be applied on the inside of the blender to prevent adhesion of the metal powder on the inner wall surface of the blender. By this technique, the particles of the pulverized metal powder become coated with the oil, so that the next pulverizing process can be smoothly performed. The coating also protects the metal powder, for a short period of time, against the reduction reaction which occurs when water is sprayed. The olive oil or similar substance applied on the inside of the blender also prevents spontaneous ignition of sodium in the process of producing the reduction treatment agent.

b) A mixed-oxide powder is prepared by adding, to the aforementioned mixed powder, an oxidized water with a pH of 2 to 3 and an ORP of 1000 mV or higher, and subsequently removing the water from the powder. In the case of mixing one or more kinds of metal other than magnesium and zinc, each kind of metal should be mixed in an amount of one part for 80 parts of magnesium, 15 parts of zinc and 30 parts of calcium.

c) A mixed organic acid is prepared by mixing calcium, ascorbic acid, citric acid and salt, 30 parts each.

d) The mixed-oxide powder and the mixed organic acid are mixed together in a ratio within a range of 20:80 to 40:60, to obtain an ionized mixture.

e) A soft lump of the ionized mixture is created by filling a mold with the ionized mixture, spraying water on its surface, and leaving it intact.

f) A hard lump of the ionized mixture is created by pressing the soft lump of the ionized mixture while heating the soft lump at a temperature of 100° C. to 200° C.

g) The hard lump of the ionized mixture is pulverized into powder to obtain a reduction treatment agent made of a powder having a particle size within a range of 1500 to 3000 mesh.

In the previously described method for producing a reduction treatment agent, the mixture ratio of the mixed-oxide powder to the mixed organic acid should preferably be within a range of 20:80 to 40:60. If this ratio is controlled to be within a range of 10:90 to 6:94, a reduction food known for its citric acid cycle will be obtained. Citric acid is capable of eliminating unwanted substances (e.g. lactic acid, uric acid, body fat, blood sugar or uremic toxin) by its chelate effect and converting those substances into energy. Another possible application is a supplement having a reduction power due to the chelate effect which helps the absorption of vitamins as well as calcium and other minerals. In this case, it is important to reduce the amount of salt in the mixed organic acid. In the case of a face-wash water or bath agent, the same mixture ratio as applied to the reduction treatment agent can be used. A cooking salt containing reduced calcium can be obtained by using, as the ingredients, 80 to 90 parts of the mixture of calcium (30 parts), salt (60 parts), citric acid (15 parts) and ascorbic acid (5 parts) as well as 20 to 10 parts of the mixed-oxide powder of magnesium and zinc. The presence of magnesium helps the absorption of calcium, in conjunction with the citric acid which enables an even more efficient absorption of calcium by its chelate effect.

The reduction treatment agent according to the present invention can be used as a freshness-keeping agent for plants, fruits or the like, as well as a cosmetic or a washing agent for clothes. In particular, when used as a cosmetic, the present invention produces various favorable effects, such as the improvement of the skin quality, tightening the facial skin or reducing the skin dullness. It should be noted that face-wash agents are included in the "cosmetics" in the present specification.

Advantageous Effects of the Invention

The reduction treatment agent according to the present invention is made of extremely fine metallic particles having a particle size within a range of 1500 to 3000 mesh and can be easily mixed with various substances. Even if the target substance is not water, the agent can entirely and uniformly change the target substance into a reduced state. Additionally, the reduction treatment agent can act as a surfactant, and therefore, can be used as cosmetics or food.

DESCRIPTION OF EMBODIMENTS

Figure 1A:
FIGS. 1A and 1B show an example in which the reduction treatment agent according to the present invention was used as a freshness-keeping agent.

The reduction treatment agent according to the present invention is obtained by pulverizing an alloy into a powder having a particle size within a range of 1500 to 3000 mesh, where the alloy is obtained by adding calcium, ascorbic acid, citric acid and salt to a mixed-oxide powder of magnesium and zinc.

Specifically, the agent can be produced by the following procedure:

(1) Magnesium (80 parts) and zinc (20 parts), each having a particle size of 200 to 400 mesh, are mixed together to obtain a mixed powder.

(2) The mixed powder is mixed with an oxidized water having a pH of 2 to 3 and an ORP of 1000 mV or higher, and is subsequently dried to obtain a mixed-oxide powder.

(3) Calcium, ascorbic acid, citric acid and salt, each prepared in an amount of 30 parts, are mixed together to obtain a powder of mixed organic acid. The salt used in this step should preferably be native salt.

(4) The mixed-oxide powder (20-40 parts) and the mixed organic acid powder (60-80 parts) are mixed together to obtain an ionized mixed powder. Subsequently, this powder is placed in a stainless-steel mold. After water is sprayed onto its surface, the powder is left intact. As a result, a comparatively brittle lump of ionized mixture is obtained. The amount of water needs to be carefully controlled, because spraying an excessive amount of water prevents the formation of the lump.

(5) The lump of the ionized mixture is further left intact. When the water content in the mixture has been decreased, the mixture is pressed while being heated to a temperature of 100° C. to 200° C. As a result, a comparatively soft yet solid lump of ionized mixture is obtained. This lump is subsequently pulverized into a powder with a particle size within a range of 1500 to 3000 mesh to obtain the reduction treatment agent.

The composition of the reduction treatment agent according to the present invention has been derived from that of ash or lye. Ash and lye are useful natural chemicals which have been used since ancient times for various purposes, such as a catalyst, contaminant remover, bleach, combustion catalyst, scum remover, detergent, disinfectant, fertilizer, or an agent for suppressing the multiplication of unwanted bacteria. It is said that soap was first discovered when tallow fell onto an amount of ash and was hydrolyzed into a fatty acid salt.

Ash is principally composed of potassium, magnesium and calcium, with other minor constituents including zinc, iron, aluminum, sodium and copper. Dissolving ash in water produces potassium carbonate ($K_2CO_3$), forming a strong alkaline solution. Accordingly, the present inventors have included these substances in the reduction treatment agent according to the present invention.

In recent years, it is difficult to procure safe types of ash due to the content of dioxin, application of chemical substances (e.g. agricultural chemicals) or influence of environmental pollution. The reduction treatment agent according to the present invention is free from such worrisome factors.

When the reduction treatment agent is mixed in water or a water-containing substance, the reduction treatment agent in the highly oxidized state releases electrons, whereby active hydrogen is generated. The generated active hydrogen causes the reduction of substances in a comparatively short period of time. A substance in a reduced state presents less of a burden on living organisms. Accordingly, utilizing drinking water or food treated with the reduction treatment agent produces favorable effects on living organisms.

With its reducing action, the reduction treatment agent according to the present invention can decompose contaminants which are adhered to clothes or similar articles. Therefore, the reduction treatment agent according to the present invention can also be used as a washing agent for clothes. Needless to say, it is not only suitable for washing clothes but can also be used as a dishwashing agent or cleaning agent.

In this case, the reduction treatment agent should preferably contain various sizes of particles ranging from 1500 to 3000 mesh. In particular, it is preferable to prepare the particles so that their particle size gradually changes at a constant rate, with each size of particles contained at the same percentage. Such a configuration makes the hydrogen generation and reduction reaction occur in a stepwise manner, so that the effective state of reduction will be maintained for a long period of time. In the experiments, which will be hereinafter described, a reduction treatment agent composed of powder particles which are roughly divided into small, medium and large sizes was used.

Hereinafter, the results of various experiments performed for the reduction treatment agent obtained by the previously described procedure will be described.

Experiment 1

The reduction treatment agent (0.4 g) was placed in 250 mL of tap water (water temperature 13° C., pH 7.8 and ORP 560 mV) and stirred. After approximately 5 seconds, a strong reduction water with a pH of 11.8 and an ORP of −780 mV was obtained. This reduction water was exposed to air for eight hours, but no change in the ORP was observed. After the passage of eight hours, the water gradually underwent oxidation. However, even after 24 hours, the ORP was at −60 mV and the water maintained the reduced state.

This result demonstrates that the aforementioned reduction treatment agent can maintain the reduced state for a longer period of time than the reduction powder described in Patent Literature 6. The reduction powder relies on the use of large particles of magnesium to maintain its ORP. The use of magnesium as a principal constituent also requires the water temperature to be 20° C. or higher so that the reaction can easily occur. By comparison, the aforementioned reduction treatment agent having a comparatively high percentage of calcium (which is easier to be ionized than magnesium) can generate hydrogen in a shorter period of time even at a low water temperature of 10° C. The decrease in the ORP is also quicker.

Since the completed reduction treatment agent is composed of particles in a stepwise manner with small, medium and large sizes, the hydrogen is generated in a sequential fashion, whereby the ORP is maintained. The reaction proceeds in descending order of ionization tendency, from calcium through magnesium to zinc.

When 0.1 g, 0.2 g, and 0.3 g of the reduction treatment agent were individually added to 250 mL of water, the ORP of the water was −250 mV, −480 mV and −680 mV, respectively. This result demonstrates that the ORP value can be freely controlled by changing the amount of the reduction treatment agent.

After being left intact for eight hours, the strong reduction water with an ORP of −780 mV was stored in a glass bottle in order to prevent its oxidization. The bottle was completely filled with the strong reduction water and covered with the lid to prevent the water from being in contact with air. After being left intact for 24 hours, the water had an ORP of −790 mV. Two days later, the ORP was at −800 mV. One week later, the ORP was at −815 mV. One month later, the ORP was at −828 mV. Six months later, the ORP was at −850 mV.

It is natural that a reduction water which is stored without being exposed to air maintains its ORP. A probable reason for the continued decrease in the ORP is because the reduction reaction by the mineral powder in the water occurs sequentially. This is the likely reason why the reduction treatment agent of the present invention maintains the reduction power for a longer period of time than the reduction powder.

The strong reduction water which had been confined in the sealed glass bottle for six months was subsequently exposed to air and left intact for one month. As a result, the ORP increased to +180 mV, which further increased to +190 mV two months later. The reason why the ORP did not reach the so-called intermediate ORP value of +200 mV even after the exposure to air is because reduced minerals produced by the reduction of the oxidized mineral particles were present in the water. This result supports the idea that the reduction treatment agent of the present invention can be a substitute for an anti-oxidant contained in food or similar kinds of substances.

Experiment 2

A reduction water with a pH of 7 was prepared by placing an acidic substance in a reduction water with an ORP of −780 mV. In this reduction water and tap water, the following objects were immersed and left intact: (1) a plant which had withered, (2) dried kelp ("kombu"), (3) dried black beans and rice grains, and (4) dried mushrooms ("shiitake"). The result was as follows:

(1) After approximately ten minutes, the plant immersed in the reduction water was revived. By comparison, the one immersed in the tap water was slightly but not fully revived.

(2) After 30 minutes, the kelp immersed in the reduction water became greenish from its original black color. It was soft when chewed. By comparison, the one immersed in the tap water remained black. It was not so soft when chewed, nor was it possible to bite off a piece.

(3) After being immersed in the reduction water for approximately one hour, the rice grains became whitish and slightly swollen. The black beans, which originally had a wrinkly rind, became smoother on their surfaces. By contrast, the black beans and rice grains immersed in the tap water were almost unchanged, with only a slight change in their appearance. The two groups of ingredients were subsequently cooked. As a result, the ingredients in the reduction water became soft, whereas those immersed in the tap water could not be cooked to be satisfactorily soft. Furthermore, those immersed in the reduction water were tastier.

(4) After approximately three minutes, the mushrooms immersed in the reduction water began to produce a strong flavor of "shiitake". After ten minutes, they had already been softened. By comparison, the one immersed in the tap water remained hard even after ten minutes.

Additionally, water-extracted coffee and water-extracted green tea were made using the reduction water. Both could be quickly extracted. By comparison, the tap water required a longer period of time for the extraction of coffee and green tea. These results demonstrate that the reduction water is more penetrative and has a higher extraction power than the tap water.

<Experiment 3>

The reduction treatment agent (20%) was mixed with vitamin E oil (40%) and tap water (40%). They could be readily mixed together and were not separated even after the mixture was left intact for six months. A similar result was obtained in an experiment in which the reduction treatment agent was mixed with each of the following ingredients: butter and tap water; chocolate and tap water; tempura oil and tap water; as well as egg yolk, olive oil and tap water. These results confirm that the reduction treatment agent of the present invention can act as a surfactant.

Experiment 4

A dish stained with oil was washed with a reduction water having an ORP of −700 mV prepared using the reduction treatment agent of the present invention. The oily stain was completely removed and the dish became clean.

A severely stained ventilation fan was cleaned by directly sprinkling the reduction treatment agent of the present invention onto the fan and washing it with a scrubbing brush soaked with water. The stain was completely removed.

A stained collar of a white shirt was cleaned by sprinkling the reduction treatment agent of the present invention onto the collar after moistening it with water, and then gently rubbing the collar with a person's fingers or the like. As a result, the stain was completely removed. Yellowed areas of the collar were also bleached. The proteins and fatty acids adhered to a collar are in the form of layers of stains and cannot be easily removed by detergents. The present invention effectively worked even for such stains. This result confirms that the reduction treatment agent of the present invention can act as a surfactant, soap (washing agent) or bleach.

<Additional Matters>

Normally, strong acidic water with a high ORP has a strong disinfecting power and has been used as disinfecting water. Strong alkaline water with a low ORP also has a strong disinfecting power and has been similarly used. For example, if 0.5 g of the reduction treatment agent of the present invention is dissolved in 250 mL of tap water, a reduction water with a pH of 12.9 and an ORP of −820 mV is obtained, which has a high disinfecting power. Dissolving 0.7 g of the reduction treatment agent results in a pH of 16 and an ORP of −980 mV, which means an even higher amount of disinfecting power. Accordingly, the reduction treatment agent of the present invention can be a substitute for a disinfectant or preservative. If water with a pH of approximately 7 or acidic water with a pH of 5 is needed, the pH can be adjusted by adding an acidic substance to the water after the reduction treatment agent of the present invention is sufficiently dispersed.

From the previously described results, it is likely that the reduction treatment agent of the present invention also has the following effects:

(1) An occurrence or progress of tooth decay, as well as the blood oozing from the gums or the stomatitis can be prevented or suppressed by brushing the teeth using the reduction treatment agent of the present invention in place of toothpaste.

(2) Sickness or hangover from drinking can be eased by dissolving the reduction treatment agent of the present invention in alcoholic drinks.

(3) Chemical components contained in agricultural chemicals can be decomposed. This effect can be confirmed from the fact that, if water with the reduction treatment agent of the present invention dissolved is sprayed onto a plant to which an agricultural chemical has been applied, the bug-repelling effect disappears after a period of time.

(4) A wound can be disinfected and cured by the zinc powder contained in the reduction treatment agent of the present invention.

(5) Favorable effects can be obtained when tempura is fried in tempura oil containing the reduction treatment agent of the present invention (for example, the tempura can be fried crisp and will retain its crispness without being oily even after it is cooled). This is due to the fact that the reduction treatment agent of the present invention can act as a surfactant and maintain its action for a long time.

(6) Mold growth in a food that is susceptible to mold growth can be prevented by previously mixing the reduction treatment agent of the present invention in the food.

In summary, the reduction treatment agent of the present invention has a strong penetration power. It has the effect of removing stains composed of fatty acids and proteins, the function of a kind of surfactant, the disinfecting effect, the effect of decomposing toxic chemical substances, as well as the bleaching effect. It can be substituted for conventionally used chemical substances, such as a surfactant, anti-oxidant, reductant, penetrant, preservative, disinfectant, bleach and detergent.

Specific examples in which the reduction treatment agent according to the present invention was used as the freshness-keeping agent, washing agent or cosmetic are hereinafter described.

First Example

The freshness-keeping effect for a plant by the addition of the reduction treatment agent to tap water was investigated.

Initially, two containers, each holding 250 mL of tap water, were prepared, with 0.3 g of the reduction treatment agent added in one of them. A plant which had withered was placed in each container. The state of the plants was observed immediately after the placement as well as ten minutes after the placement.

Figure 1B:

FIG. 1A is a photograph showing the state of the plants immediately after the placement, while FIG. 1B is one showing their state after ten minutes. In each photograph, the bottle on the left contains the tap water with the reduction treatment agent added, while the bottle on the right contains the tap water without the additive. Both the plant placed in the tap water with the reduction treatment water added and the one placed in the tap water without the additive were revived after the passage of ten minutes. However, as can be seen in the photographs, the plant placed in the tap water with the reduction treatment water added was more noticeably revived than the one placed in the tap water without the additive.

Second Example

Figure 2A:
FIGS. 2A and 2B show an example in which the reduction treatment agent according to the present invention was used as a washing agent for clothes.
Figure 2B:

In order to investigate the washing effect of the reduction treatment agent according to the present invention, the reduction treatment agent of the present invention was sprinkled onto a stained collar of a white shirt (FIG. 2A) after moistening the collar with water. By gently rubbing the collar with a brush, the contaminants could be completely removed and the collar became clean, as shown in FIG. 2B.

Third Example

Figure 3:
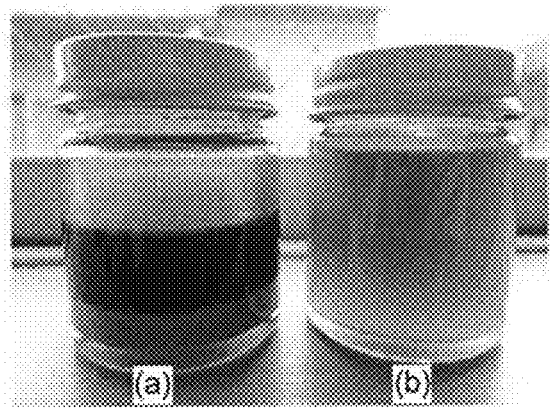
FIG. 3 shows an example in which the reduction treatment agent according to the present invention was used as a surfactant, where (a) shows the state of vitamin E oil with the reduction treatment agent added, and (b) shows the state of a mixture of vitamin E oil and water with the reduction treatment agent added.

Two grams of the reduction treatment agent according to the present invention was placed in 20 mL of vitamin E oil. The mixture was stirred and left intact. As a result, the reduction treatment agent was settled ((a) in FIG. 3). By comparison, when 10 mL of water was additionally mixed and stirred in 20 mL of vitamin E oil along with 2 g of the reduction treatment agent according to the present invention, the vitamin E oil was not separated from the reduction treatment agent and water even after the mixture was left intact for six months ((b) in FIG. 3).

Fourth Example

The reduction treatment agent produced by the previously described procedure was applied as cosmetics on ten subjects to test its effect. It should be noted that the reduction treatment agent was mixed with some other components for each use case, as will be hereinafter described.

[Subject No. 1]

A woman, in her 50s, with sensitive skin. Use period, approximately one and a half months.

Five days a week (Monday through Friday), she applied a mixture of moisturizing lotion (10 mL), vitamin E oil (2-3 mL) and reduction treatment agent (0.3-0.4 g) to her facial skin every morning and night. The other two days (Saturday and Monday), she applied a mixture of water and reduction treatment agent mixed in a ratio of approximately 5:1 to her facial skin before going to bed. As a result, the skin quality gradually improved. Additionally, she also felt that her skin was refreshed. The skin texture became smoother, as well as healthier and more resilient.

[Subject No. 2]

A man, in his 70s. Use period, approximately one and a half months.

He tried a sample prepared by mixing 2-3 mL of vitamin E oil and *Macadamia ternifolia* (in a ratio of 6:4) with 10 mL of moisturizing lotion and 0.3-0.4 g of reduction treatment agent. He applied it to the right half of his face every morning and night. Approximately one month later, a third-party person pointed out that the area to which the sample had been applied (right half of the face) looked tightened. After having continued applying the sample for approximately 40 days, he discontinued applying it. Instead, he began to take a mixture of food vitamin E oil and reduction treatment agent (in a ratio of 1:1) every day, using a commercially available capsule (size #00) as a container for the mixture. After about ten days from the beginning of the intake of the capsule, a third-party person (a woman who had not seen him for a long time) told him that his skin had become glossy and clean. The subject also felt that his skin had become more moisturized than before.

[Subject No. 3]

A woman, in her late 50s. Use period, approximately 40 days.

She had a spot on her cheek near one of her eyes, which had emerged approximately six months earlier. She also had many dull areas on her face. She applied a mixture of 10 mL of cosmetic cream and 3 g of reduction treatment agent to the spot and dull areas. Additionally, she covered the area of the spot with a mixture of a mineral foundation powder and the reduction treatment agent. After approximately 40 days from the beginning of use, the spot and dull areas were considerably paler than before.

[Subject No. 4]

A man, in his early 60s. A one-time use.

He used a liquid soap in which the reduction treatment agent was mixed by 20-30%. He washed one of his hands with this mixture and the other hand with a conventional soap. As a result, the soap with the reduction treatment agent mixed showed a stronger washing power. An overall whitening effect was also obtained.

[Subject No. 5]

A woman, in her late 40s, with sensitive skin easy to react to or smart from cosmetics. Use period, approximately 40 days.

She had previously drunk reduction water for the sake of health improvement.

However, no improvement in her skin quality had been achieved. She applied a sample of water with the reduction treatment agent mixed at 20-30% to the skin in place of a lotion after face washing. For the daytime, she continued using a blend of lotion, reduction treatment agent, *Macadamia ternifolia* and vitamin E oil (the same mixture as prepared for Subject No. 2). As a result, her skin became less sensitive and less likely to smart from cosmetics. The skin texture also became smoother.

[Subject No. 6]

A woman, in her late 50s. Use period, approximately 10 days.

She had long suffered from dry skin. Particularly in winter, the dryness caused her skin to crack. She used a moisturizing lotion, filtered water, oil and reduction treatment agent mixed in a ratio of 10:3:1:1 as a body lotion for ten days. Consequently, her skin was relieved of its terrible dryness and became comfortably moisturized. She was also pleased with her entire body having become radiant. She also applied the mixture to her facial skin, whereby the dryness was similarly alleviated. The consumption of the body lotion gradually decreased.

[Subject No. 7]

A man, in his early 70s. Use period, approximately 30 days.

He applied a mixture of 3 mg of reduction treatment agent and 10 mL of cosmetic cream to a spot at the nasal root every morning and night. After approximately 30 days from the beginning of use, the spot was considerably paler than before.

[Subject No. 8]

A woman, in her 50s. Use period, approximately one and a half months.

She tried a moisturizing lotion, oil, and reduction treatment agent mixed in a ratio of 10:1:1. After a few days of use, she really felt her face had become firmer. A further continued use resulted in her facial skin having fewer fine wrinkles, a softer surface and generally smoother texture. Liver spots around the cheekbones began to be paler, with their redness considerably faded. People around her said that her facial shape appeared to have changed. A likely reason for this is because the entire face became firmer due to the tightening effect. After approximately one and a half months of use, her face had a radiance and a one-tone fairer complexion.

[Subject No. 9]

A woman, in her 70s. Use period, approximately ten days.

She tried a moisturizing lotion, oil, and reduction treatment agent mixed in a ratio of 10:1:1. When she washed her face for the first time after the beginning of use, she felt that the dirt on her skin was removed more quickly than usual. Additionally, it seemed to her that she had a slightly fairer complexion. Touching her cheeks with both hands gave the feel of a change in the contour. The face seemed to have become slightly smaller.

[Subject No. 10]

A woman, in her 50s. Use period, approximately ten days.

She tried reduction water, oil, and reduction treatment agent mixed at a ratio of 10:1:1. After two days from the beginning of use, she felt that her face had been tightened, with the skin being seemingly firmer. Her entire face appeared to have been pulled up. After she continued using it every morning and night, the skin color also seemed to have become slightly fairer. The entire face gave the impression of having become cheerful.

Magnesium is a substance which generates a large amount of hydrogen and thereby contributes to the lowering of the ORP. Zinc is a substance which generates hydrogen at a lower rate than magnesium, thereby contributing to both the lowering of the ORP and the maintenance of the ORP. Calcium is a substance which lowers the ORP even in a small quantity. The metallic powders other than magnesium and zinc contribute to the lowering of the ORP to a certain extent. To confirm these facts, an experiment was conducted. The result was as shown in Tables 1 and 2 below.

TABLE 1

| Elapsed Time | 1 min. | 2 min. | 3 min. | 4 min. | 5 min. |
|---|---|---|---|---|---|
| ORP | +81 | −110 | −650 | −720 | −745 |

TABLE 2

| Elapsed Time | 5 sec. | 10 sec. | 20 sec. | 30 sec. | 1 min. | 5 min. | 1 hr. | 6 hr. | 12 hr. |
|---|---|---|---|---|---|---|---|---|---|
| ORP | −495 | −580 | −685 | −720 | −750 | −755 | −757 | −758 | −759 |

Table 1 shows a change in the ORP of a solution obtained by dissolving, in 250 mL of water, 0.3 g of a mixture of the aforementioned mixed organic acid (calcium, ascorbic acid, citric acid and salt) and the aforementioned mixed-oxide powder (magnesium and zinc). Table 2 shows a change in the ORP of a solution obtained by dissolving, in 250 mL of water, 0.3 g of a mixture of the mixed organic acid with calcium removed and the mixed-oxide powder. The "time" in these (and subsequent) tables shows the elapsed time from the point of dissolution. As is evident from the comparison between Tables 1 and 2, the solution which did not contain calcium showed a faster decrease in the ORP. However, after five minutes from the point of dissolution, both solutions had approximately equal ORP values.

TABLE 3

| Elapsed Time | 1 hr. | 3 hr. | 6 hr. | 12 hr. | 24 hr. | 36 hr. | 48 hr. | 60 hr. | 72 hr. |
|---|---|---|---|---|---|---|---|---|---|
| ORP | +322 | +115 | −65 | −151 | −162 | −198 | −245 | −365 | −366 |

TABLE 4

| Elapsed Time | 5 sec. | 10 sec. | 20 sec. | 30 sec. | 1 min. | 5 min. | 1 hr. | 6 hr. | 12 hr. |
|---|---|---|---|---|---|---|---|---|---|
| ORP | −127 | −577 | −671 | −682 | −740 | −128 | −98 | −60 | +115 |

Table 3 shows a change in the ORP of a solution obtained by dissolving, in 250 mL of water, 0.3 g of a mixture of the aforementioned mixed-oxide powder with magnesium removed and the aforementioned mixed organic acid. Table 4 shows a change in the ORP of a solution obtained by dissolving, in 250 mL of water, 0.3 g of a mixture of the aforementioned mixed-oxide powder with zinc removed and the aforementioned mixed organic acid. A comparison between Tables 1 and 3 demonstrates that the solution with magnesium removed requires a longer period of time for the ORP to be lowered. A comparison among Tables 1, 3 and 4 demonstrates that the solution with zinc removed does not delay the decrease in the ORP so much as the solution with magnesium removed. However, its ORP value begins to increase in a comparatively early phase after the temporary decrease. This result demonstrates that zinc contributes to the maintenance of the decreased ORP.

TABLE 5

| Elapsed Time | 5 sec. | 10 sec. | 20 sec. | 30 sec. | 1 min. | 5 min. | 1 hr. | 6 hr. | 12 hr. |
|---|---|---|---|---|---|---|---|---|---|
| ORP | −499 | −590 | −699 | −730 | −755 | −765 | −758 | −760 | −760 |

Table 5 shows a change in the ORP of a solution obtained by dissolving, in 250 mL of water, 0.3 g of a mixture of the aforementioned mixed organic acid and a mixed-oxide powder which was prepared by mixing an oxidized water (with a pH of 2-3 and an ORP of 1000 mV or higher) in a blended powder of magnesium (80 parts), zinc (15 parts), calcium (30 parts) as well as copper, molybdenum, nickel, cobalt, iron and aluminum (one part each). A comparison between Tables 1 and 5 demonstrates that the sample in which the metal powder other than magnesium and zinc was mixed showed a slightly greater amount of decrease in the ORP after the passage of five minutes than the sample with no such metal powder mixed.

Tables 6 and 7 respectively show the results of an X-ray analysis and fluorescent X-ray analysis performed for the substance used in the experiment which yielded the result shown in Table 5.

TABLE 6

| Sodium Hydrogen Carbonate | Sodium Carbonate | Magnesium | Calcium | Zinc |
|---|---|---|---|---|
| ◎ | ◎ | ○ | Δ | Δ |

TABLE 7

| Detected Element | C | O | Na | Mg | Zn | Ca |
|---|---|---|---|---|---|---|
| Semi-quantitative Value (wt %) | 12.8586 | 61.3693 | 23.6937 | 1.9196 | 0.0606 | 0.0982 |

The result shown in Table 6 revealed that sodium carbonate and sodium hydrogen carbonate were formed in the substance used in the experiment which yielded the result shown in Table 5. It is likely that the sodium carbonate and sodium hydrogen carbonate were formed from ascorbic acid, citric acid and salt (NaCl). Based on this result, another experiment was conducted as follows: Six grams of a mixed powder of magnesium (80 parts), zinc (15 parts), calcium (30 parts) as well as copper, molybdenum, nickel, cobalt, iron and aluminum (one part each) was mixed with 100 g of a mixed powder of sodium carbonate and sodium hydrogen carbonate (50 parts each). The obtained powder ("mixed powder") was pulverized into large, medium and small particles ranging from 1500 to 3000 mesh. One gram of the obtained particles were dissolved in 3 L of water, and the ORP was measured. The result was as shown in Table 8. From Table 8, it was confirmed that the reduction treatment agent can also be created by this method, although the amount of decrease in the ORP is not so large.

TABLE 8

| Elapsed Time | 5 sec. | 20 sec. | 1 min. | 5 min. | 1 hr. | 6 hr. | 12 hr. | 24 hr. | 36 hr. |
|---|---|---|---|---|---|---|---|---|---|
| ORP | −288 | −299 | −305 | −356 | −325 | −309 | −289 | −205 | −115 |

Though the result is not shown, adding only 100 g of sodium carbonate or 100 g of sodium hydrogen carbonate to 6 g of the mixed metallic powder containing calcium also produced a similar result to the one obtained in the case where both substances were added. Mixing either sodium carbonate or sodium hydrogen carbonate in a mixed metallic powder containing magnesium, zinc and calcium also produced a similar result.

It was also experimentally confirmed that the previously described reduction treatment agent can act as a surfactant. It was also confirmed that the reduction treatment agent according to the present invention can be used as citric acid reduction food or reduction cooking salt by adjusting the amounts of contained substances.

The invention claimed is:

1. A reduction treatment agent, consisting of a powder with a particle size within a range of 1500 to 3000 mesh, the powder consisting of:
   a) 6 to 12 parts of a mixed powder consisting of magnesium oxide, zinc oxide and calcium;
   b) 50 parts of sodium hydrogen carbonate;
   c) 50 parts of sodium carbonate; and
   d) one to six kinds of metal powder selected from the group consisting of copper, molybdenum, nickel, cobalt, iron and aluminum, each in an amount of one part.

2. A reduction treatment agent, consisting of a powder with a particle size within a range of 1500 to 3000 mesh, the powder consisting of:
   a) 6 to 12 parts of a mixed powder consisting of magnesium oxide, zinc oxide and calcium;
   b) 50 to 200 parts of sodium hydrogen carbonate or sodium carbonate; and
   c) one to six kinds of metal powder selected from the group consisting of copper, molybdenum, nickel, cobalt, iron and aluminum, each in an amount of one part.

3. A method for producing a reduction treatment agent, comprising the following steps:
   a) pulverizing 80 parts of magnesium, 30 parts calcium, and 15 parts of zinc and one to six kinds of metal powder selected from the group consisting of copper, molybdenum, nickel, cobalt, iron and aluminum, each in an amount of one part, into a mixed powder with a particle size of 200 to 400 mesh;
   b) preparing a mixed-oxide powder by adding, to the aforementioned mixed powder, an oxidized water with a pH of 2 to 3 and an ORP of 1000 mV or higher, and subsequently removing the water from the powder;
   c) preparing a mixed organic acid by mixing calcium, ascorbic acid, citric acid and sodium chloride, 30 parts each;
   d) mixing the mixed-oxide powder and the mixed organic acid together in a ratio within a range of 20:80 to 40:60, to obtain an ionized mixture;
   e) creating a soft lump of the ionized mixture by filling a mold with the ionized mixture, spraying water on a surface of the ionized mixture, and leaving the ionized mixture intact;
   f) creating a hard lump of the ionized mixture by pressing the soft lump of the ionized mixture while heating the soft lump at a temperature of 100° C. to 200° C.; and
   g) pulverizing the hard lump of the ionized mixture into powder to obtain a reduction treatment agent consisting of a powder with a particle size within a range of 1500 to 3000 mesh, the powder consisting of:
      a) 6 to 12 parts of a mixed powder consisting of magnesium oxide, zinc oxide and calcium;
      b) 50 to 200 parts of sodium hydrogen carbonate or sodium carbonate; and
      c) one to six kinds of metal powder selected from the group consisting of copper, molybdenum, nickel, cobalt, iron and aluminum, each in an amount of one part.

4. A reduction cosmetic, comprising a reduction treatment agent consisting of a powder with a particle size within a range of 1500 to 3000 mesh, the powder consisting of:
   a) 6 to 12 parts of a mixed powder consisting of magnesium oxide, zinc oxide and calcium;
   b) 50 parts of sodium hydrogen carbonate; and
   c) 50 parts of sodium carbonate; and
   d) one to six kinds of metal powder selected from the group consisting of copper, molybdenum, nickel, cobalt, iron and aluminum, each in an amount of one part.

5. A reduction cosmetic, comprising a reduction treatment agent consisting of a powder with a particle size within a range of 1500 to 3000 mesh, the powder consisting of:
   a) 6 to 12 parts of a mixed powder consisting of magnesium oxide, zinc oxide and calcium; and
   b) 50 to 200 parts of sodium hydrogen carbonate or sodium carbonate; and
   c) one to six kinds of metal powder selected from the group consisting of copper, molybdenum, nickel, cobalt, iron and aluminum, each in an amount of one part.

* * * * *